(12) United States Patent
Horian

(10) Patent No.: US 8,813,759 B1
(45) Date of Patent: Aug. 26, 2014

(54) NICOTINE INHALER AND METHOD OF MANUFACTURE

(76) Inventor: Richard C. Horian, Corona, CA (US)

( * ) Notice: Subject to any disclaimer, the term of this patent is extended or adjusted under 35 U.S.C. 154(b) by 433 days.

(21) Appl. No.: 12/949,605

(22) Filed: Nov. 18, 2010

(51) Int. Cl.
*A61M 15/06* (2006.01)
*A24F 47/00* (2006.01)

(52) U.S. Cl.
USPC ........................................ 131/273; 128/202.21

(58) Field of Classification Search
CPC ......... A24F 47/02; A24F 47/00; A61M 15/05
USPC ................ 131/270, 273; 128/202.21
See application file for complete search history.

(56) References Cited

U.S. PATENT DOCUMENTS

| 2,445,476 | A | * | 7/1948 | Folkman | 131/273 |
| 2,860,638 | A | * | 11/1958 | Bartolomeo | 128/202.21 |
| 4,273,142 | A | * | 6/1981 | Swanson et al. | 131/339 |
| 2004/0041302 | A1 | * | 3/2004 | Siferd et al. | 264/295 |
| 2004/0055613 | A1 | * | 3/2004 | Horian | 131/194 |
| 2006/0191546 | A1 | * | 8/2006 | Takano et al. | 131/270 |

* cited by examiner

*Primary Examiner* — Richard Crispino
*Assistant Examiner* — Eric Yaary
(74) *Attorney, Agent, or Firm* — Novak Druce Connolly Bove + Quigg LLP

(57) ABSTRACT

A self contained, hermetically sealed, cigarette shaped nicotine inhaler tube includes a cylindrical wall and formed closed ends. The two or more elements making up the tube are formed and sealed together after forming at a location between the closed ends, capturing a filler within. The filler is in the tube to carry nicotine. The closed ends are recessed from the end of the cylindrical tube and may be truncated conically shaped. The closed ends may be drawn further into the tube using heat and the pressure of a probe. A tool for piercing the ends of the tube includes a supportive cylindrical cavity slightly larger than the tube with a centric spike and a terminal surface in the cavity. The cylindrical wall of the tube is supported by the cavity and the truncated conical shape of the end wall to receive the spike for penetrating the end wall at each end. The terminal surface prevents excessive penetration of the spike.

10 Claims, 2 Drawing Sheets

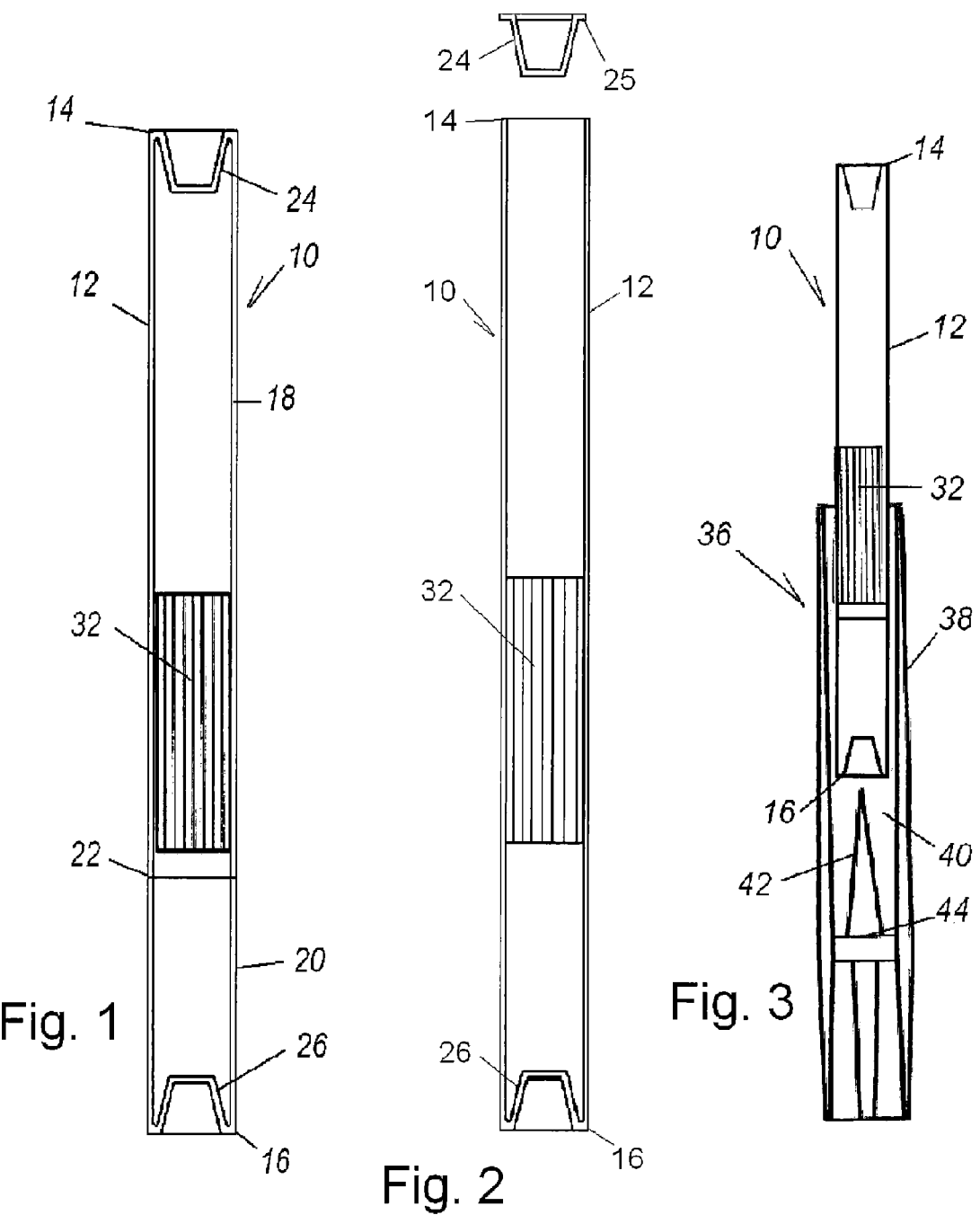

NICOTINE INHALER AND METHOD OF MANUFACTURE

BACKGROUND OF THE INVENTION

The field of invention is cigarette substitute nicotine inhaler tubes.

There are three patented concepts that define the field of invention regarding non-mechanical nicotine inhaler cigarette substitutes: U.S. Pat. No. 2,445,476 to Folkman; U.S. Pat. No. 6,769,436 to Horian and U.S. Pat. No. 5,400,808 to Turner, with continuations U.S. Pat. Nos. 5,501,236 and 6,098,632, all the foregoing Patents being incorporated herein by reference. These devices each define a self contained cigarette shaped open air tube inhaler designed to deliver evaporate to the user released from liquid nicotine contained within the tube.

It was Marvin L. Folkman (U.S. Pat. No. 2,445,476—1958) who may be first credited with the concept of a cigarette substitute meant to replace ignitable cigarettes by using liquid nicotine contained in a cigarette shaped tube and breathing air through the tube to deliver nicotine evaporate to the user. He first teaches an absorbent of tobacco or other material being placed inside an open air cigarette shaped tube then sealing the tube to prevent the escape of any vapors until used. The open air tube was to be capped with "plugs" to be removed by the user when ready for use.

Mr. Folkman's device might have been a practical and commercial success providing he would have been able to add the volatile liquid nicotine to the absorbent within the tube, ship and get the product to his customer within three days. However, the science and materials of his day would never allow his product to be adequately sealed to prevent the volatile liquid nicotine vapors from prematurely escaping within the tube to the open atmosphere before use.

If the tube is adequately sealed with a contiguous nicotine barrier material, the nicotine content can last for years. In effect, the sealed tube must be made of one continuous nicotine barrier material. However, without a hermetic seal, three days is all nature allows before the consumer will discover a tube container mostly depleted of vapor deliverables. Even today, with the advanced chemical resistant materials available, a plug or cap that will provide a friction or interference fit is not understood to exist. A hermetic seal requires a contiguous wall of barrier material. Any joint friction fit seal will fail. Only a fusion seal will contain the nicotine vapors, one where the material at the seal becomes seamlessly homogenous with the balance of the tubes chemical and pressure resistant material.

It was thought that there were only two ways to accomplish an appropriate seal. Turner teaches:

> . . . a self-sealed, nicotine impermeable barrier enclosing the nicotine reservoir, said barrier including at least one nicotine barrier layer formed essentially of a copolymer effective in deterring nicotine migration; the barrier layer including at least two adjacent surfaces heat sealed to form a continuous nicotine impermeable barrier so that the nicotine can be prevented from migration outside the barrier.

Simply, the Turner device has an open air tube with a "layer" meaning a second detached piece being sealed over the face of the opening at each end of the tube. This means that there must be a container of three or more pieces to be viable; the tube itself and the "layer" for each end of the open tube consisting of one or more layers included with the laminate being heat fused over the openings to accomplish closure and a "continuous nicotine impermeable barrier."

The Horian patent taught the second way to accomplish a sealed liquid nicotine content tube that was a continuous nicotine impermeable barrier:

> . . . an inhaler of volatile nicotine vapor, comprising a one piece tube pinch closed and sealed at the ends thereof, the one piece tube being impermeable to nicotine; a volatile nicotine contained within the tube; and an element in tube absorbent of the volatile nicotine."

The Horian device has a container consisting of only one piece as opposed to Turner's three or more piece container.

In 2006, the Horian patent was challenged with an Inter-partes Reexamination at the United States Patent and Trademark Office. Over a period of four years, hundreds of pages of documents, including prior art patents from all over the world, were reviewed and carefully analyzed in the Reexamination. In the end, the Horian patent prevailed. It came down simply to the fact that there were only two ways to hermetically seal a nicotine content tube to become a continuous nicotine impermeable barrier. The prior technology either seals the open ends of the nicotine content tube with two or more layers of barrier material (Turner) or uses a one piece tube with pinch close heat fuse the ends (Horian).

It is important to understand why the tube sealing method and closures are so important when trying to construct a viable nicotine content, air flow inhaler. Liquid nicotine is the reason this task is so difficult to accomplish. Liquid nicotine, $C10H14N2$, is a colorless, poisonous alkaloid, derived from the tobacco plant and various vegetables such as eggplant, potatoes and tomatoes. It is the substance in tobacco to which smokers are understood to be addicted. The LD50 of nicotine is 50 mg/kg for rats and 3 mg/kg for mice. 40-60 mg can be a lethal dosage for adult human beings. This makes it an extremely deadly poison. It is more toxic than many other alkaloids such as cocaine, which has a lethal dose of 1000 mg. Nicotine is also a very tenacious substance. It will attack and or migrate through most plastic resins; even those usually designed for their chemical resistant properties. Nicotine has a vapor pressure of 0.53 MBR at 25 degrees C., surface Tension: 39.6 dyne/cm, Density: $1.032 \ g/cm^{3'}$ Flash Point: 101.7° C., and Enthalpy of Vaporization: 48.15 kJ/mol. Thus, not only is liquid nicotine a poison that can attack or migrate through many materials, it also has a vapor pressure that further complicates containment within any sealed tube to be used as a cigarette substitute intended for consumers to breath released volatile vapors.

With the difficulties of working with a nicotine content hermetically sealed container now understood, it is important to clarify precisely how the Turner and Horian patents are similar in use. Both the Turner and Horian containers are readied for use by severing or puncturing the exposed extreme ends of the container. Turner by puncturing the flat faced heat seal "barrier layer" and Horian by severing the extreme end of the pinched closed heat sealed ends.

Both methods leave the container portion that has been punctured or severed exposed to the mouth; more specifically the lips and tongue of the user. This can include jagged surfaces or burrs at the opening of the container which might cut or scratch the delicate skin surfaces of the user's mouth when contact with the container is made. Further, this places the interior of the tube immediately adjacent the mouth and tongue of the user, allowing contact with concentrated nicotine

SUMMARY OF THE INVENTION

The present invention is directed to a nicotine inhaler, its formation and a piercing tool used therewith, the inhaler including a tube sealed and impervious to nicotine having a cylindrical wall and closed ends. A filler is within the interior of the tube to carry nicotine that will allow evaporation with said evaporate being delivered to the user via inhalation. This device provides a structure which can have the feel of a cigarette and is able to retain volatile nicotine for an extended shelf life.

In a first separate aspect of the present invention, at least one end of the tube is recessed; and the ends can be pierced for use. The recess separates the end of the tube from the user's mouth. This displaces the source of nicotine and the potentially rough point of piercing a distance from the user's mouth and tongue.

In a second separate aspect of the present invention, the recess has a conical wall extending both into the tube and radially inwardly of the cylindrical tube. This can guide the user in piercing the end of the tube for use. By displacing the wall radially inwardly, liquid and filler material is trapped away from the piercing and is retained within the tube.

In a third separate aspect of the present invention, the closed ends are formed with the tube and each has a formed recess. The tube is assembled at a part line between the closed ends.

In a fourth separate aspect of the present invention, a tool having cylindrical cavity with an opening at one end, a centric spike in the cavity facing the opening and a terminal surface across the cavity provides support for a nicotine inhaler tube while piercing one end of the tube and preventing its displacement beyond that needed to create an appropriate hole. The tool may further be sized to go in a pack with nicotine inhalers.

In a fifth separate aspect of the present invention, the tube sealed and impervious to nicotine having a cylindrical wall and closed ends may employ a hot draw on the closed ends with the end walls displaced from the cylindrical wall of the tube. This formation process can thin the material and enhance the ease of opening the closed ends for use.

In a sixth separate aspect of the present invention, any of the foregoing separate aspects may be combined to further advantage.

Accordingly, objects of the present invention are to provide an improved inhaler, a tool for use with the inhaler and a method for the manufacture of the inhaler. Other and further objects and advantages will appear hereinafter.

BRIEF DESCRIPTION OF THE DRAWINGS

FIG. 1 is a cross-sectional view of a nicotine inhaler.

FIG. 2 is a cross-sectional view of a nicotine inhaler of a second construction before joining the elements.

FIG. 3 is a schematic view illustrating a tool of opening the closed ends of the nicotine inhaler of FIG. 1.

DETAILED DESCRIPTION OF THE PREFERRED EMBODIMENTS

Figure 4:
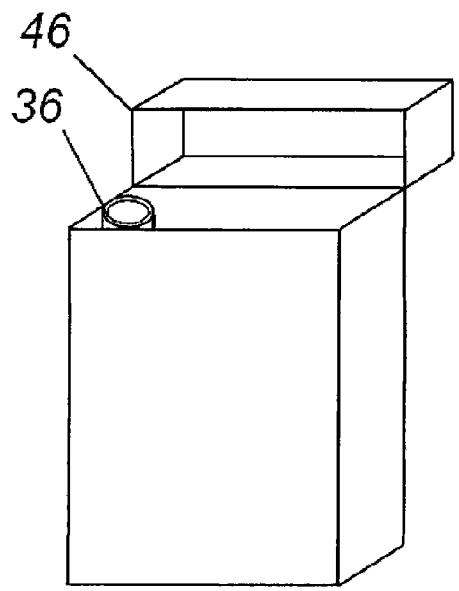
FIG. 4 is a perspective view of the placement of the tool of FIG. 3 in a pack for carrying nicotine inhalers of FIG. 1.
Figure 5:
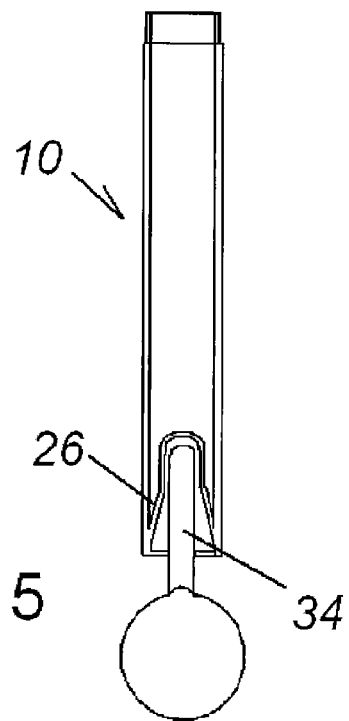
FIG. 5 schematically illustrates a hot draw to thin the end wall of a closed cylindrical portion of a nicotine inhaler.

Turning in detail to the drawings, a nicotine inhaler includes a tube 10 which is sealed and impervious to nicotine. The tube 10 has a cylindrical wall 12 and two closed ends 14, 16. The tube 10 in the embodiment of FIG. 1 is of two molded or formed cylindrical portions 18, 20 heat fused together to form a butt-weld 22. Each cylindrical portion 18, 20 is a round cylinder in shape having one open end and one closed end wall 24, 26, formed with the respective tube element 18, 20. The first cylindrical portion 18 is approximately 0.250"-0.350" in diameter and about 1" long. The second cylindrical portion 20 is approximately 2"-3" long of the same overall diameter. The wall thickness of both cylindrical portions 18, 20 can range from 0.015"-0.065" with a preferred wall thickness approximately 0.025"-0.040".

Figure 6:
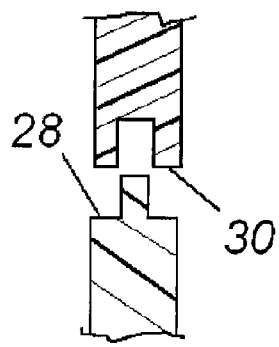
FIG. 6 illustrates a first cross-sectional detail of the open end walls of the abutting cylindrical portions of a nicotine inhaler.
Figure 7:
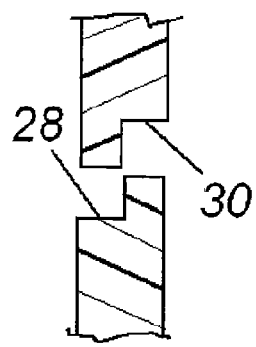
FIG. 7 illustrates a second cross-sectional detail of the open end walls of the abutting cylindrical portions of a nicotine inhaler.
Figure 8:
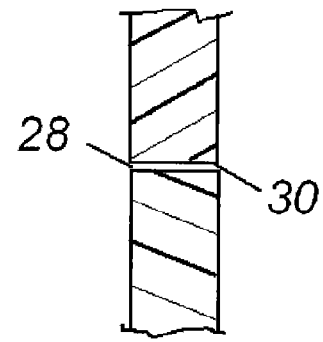
FIG. 8 illustrates a third cross-sectional detail of the open end walls of the abutting cylindrical portions of a nicotine inhaler.

The open end wall face 28, 30 of each cylindrical portion 18, 20 has one of three shapes, as illustrated in FIGS. 6-8, intended to allow the joining of the two tube elements 18, 20 together. These may be right angle wall faces, FIG. 8, to allow the cylindrical portions 18, 20 to be flush butted together, tongue and groove wall faces, FIG. 6, to retain the resulting butt-weld 22 displaced from the surface of the tube 10 or lapped end wall faces, FIG. 7, to allow an interference friction fit of the cylindrical portions 18, 20 together before welding.

The tube 10 in the embodiment of FIG. 2 is of two molded or formed portions 18A, 20A heat fused or otherwise integrated together. In this embodiment, one element is the full length of the tube 10 with one closed end wall 26. The other element of the tube 10 is a separate end wall 24 having a circular radially extending flange 25. The circular radially extending flange 25 may be heat fused, chemically fused or otherwise integrated with the open end of the cylindrical wall 12. Thus, in both the embodiments of FIGS. 1 and 2, the tube 10 is assembled from two elements at a part line between the two ends 14, 16.

The closed end walls 24, 26 of the cylindrical wall 12 are recessed inwardly of the ends 14, 16. The recess may be of a right angle shape or a conical concave shape or any other shape indented from the right angle surface. The conical shape is preferred.

To produce a hermetically sealed, self contained, cigarette substitute air flow nicotine evaporate inhaler, the following steps are taken. First, the cylindrical portions 18, 20 are molded, or formed in the embodiment of FIG. 1. In the embodiment of FIG. 2, the cylindrical element with the tube 12 and one closed end wall 26 and the separate end wall 24 are molded or formed. In each case, the molding process may include injection molding, rotational molding, extrusion, spin forming, casting and blow molding. The elements of the tube may be made of any polymer, copolymer, rubber, or other material that allows heat forming or heat sealing and is also resistant to liquid nicotine. The tube 10 may be parallel in nature or have a slight draft to facilitate molding. The tube wall 12 may have attached or included ribs or bosses to facilitate the addition and or securement of a filler 32 or the walls may be smooth bore, free of inclusions or attachments with the filler 32 friction fit within the tube 10.

A preferred embodiment of the molding or forming of the tube 10 is to use a resin known for its chemical resistance to nicotine. Barex® supplied by INEOS Barex, is one such resin as well as PEN, polyethylene naphthalate marketed by Shell and by Eastman, as well as Vectra® by Ticona and Isoplast by Dow. There are many other chemical resistant barrier plastic resins in use or currently in development that may be used for this purpose.

The filler 32 is air pervious filler and positioned inside the cylindrical wall 12 before assembly of the tube 10. The material of the filler 32 may be absorbent or non-absorbent providing it contains sufficient surface volume to capture or retain via absorption or adsorption virtually all of the liquid nicotine content solution later added and that air is able to flow around and or through the filler material to facilitate vapor transfer within the air flow of the tube 10 during use. There are literally hundreds of materials that may be used here including paper, synthetic fibers, blends or natural fibers such as cotton. Tobacco itself is an excellent absorbent that may be used in shredded form, plug, roll, reconstituted sheet tobacco, a tobacco pouch or moist tobacco.

A nicotine solution is disbursed into the filler 32 before or after introduction into the tube 10. The solution may be pure nicotine liquid or other additives or diluents may be included with the nicotine. Flavor additives, medicates or menthol may also be included. The amount of the nicotine solution added is commensurate with the filler 32. The solution added preferably does not go beyond saturation of the filler 32 to prevent liquid solution from leaking in liquid form from an opened tube 10. A preferred embodiment would be to add 1 mg to 8 mg of nicotine solution.

After the nicotine solution is added to the filler 32, the elements of the tube 10 are joined and fused to form an air and water tight joint of like contiguous material so that the tube become one. This may be accomplished by heating the end wall faces 28, or flange 25 to make them molten to allow joining, spin welding, RF welding, sonic welding, heat sealing or flaming the cylindrical portions 18, 20 together.

To use, both end walls 24, 26 are punctured to allow air to be drawn through the tube 10, picking up nicotine vapors for inhalation. The closed end walls 24, 26 of the fabricated tube 10 are recessed.

The preferred wall thickness of the tube 10 stated above is 0.025"-0.040". This is a considerable amount of material to easily puncture through to open the end walls 24, 26. Preferably, the end walls 24, 26 have a wall thickness less than 0.025" which is much more manageable for easily punching holes through to allow air flow through the tube 10. The end walls 24, 26 are no thicker than the cylindrical wall 12, a thickness of 0.040" or less, to facilitate puncture. A 0.020" or less wall thickness for the end walls 24, 26 under current molding techniques is possible and preferred.

An integral thin wall of 0.010" to 0.040" in the recessed molded area at the point of puncture is functional. However, such a thin wall is still not adequate alone for every resin material which may be used. The elderly and those with arthritis may still have trouble punching through a 0.020" plastic wall. To solve this problem, post heat pressure forming may be used. The portions 18 and 20 or 24 to be joined may be contiguously molded. The end walls 24, 26 are part of the same flow of material that comprise the cylindrical wall 12 of the tube 10 in the embodiment of FIG. 1. In either embodiment, the end walls 24, 26 are molded as thin as practical including the recessed area.

In post heat pressure forming, the end walls 24, 26 are separately heated and/or a probe 34 in the shape of a rounded end rod is heated. The probe 34 is forced against each end wall 24, 26 to draw the end wall 24, 26 inwardly of the tube 10. This process stretches the resin wall. It becomes thinner and thinner the further one stretches it from its original shape. Therefore, the end walls 24, 26 that are contiguous and integral with the rest of the tube 10 can be pressure formed further for the purposes of thinning that wall.

The end walls 24, 26 illustrated in the preferred embodiment are shown to extend inwardly from a base attachment at the ends 14, 16 of the cylindrical wall 12 and have a formed truncated conical shape. The conical shape creates a recess approximately ¼" deep. This recess can be drawn by heat pressure forming to a depth of ⅜" to ¾" making the side and bottom walls of the end face walls quite thin. Even with the end walls 24, 26 being this thin, as long as the material is a continuous flow of the rest of the molded tube part or properly bonded at the flange 25, it will remain an effective nicotine barrier seal until punctured. The conical recession additionally is tapered to a diameter less than the ID of the rest of the tube 10. This shape tapers the conical wall away from, or radially inwardly of, the cylindrical wall 12. Therefore, the conical wall can retain a loose filler 32 away for the user, capture any liquid nicotine in the tube 10 from leaking out and displace a hot probe 34 from heating or distorting the cylindrical wall 12 during the drawing operation.

The recessed feature of the end walls 24, 26 prevents a rough or cut edge from being exposed to irritate or cut a users lip or tongue during use. The punctured hole is deep below the face area of the tube end coming into personal contact during use. It is a common practice of many smokers to "tongue" the end of the cigarette. This practice entails placing the tip of the tongue on the end face wall of the cigarette to actually make contact with the cigarette's filter or tobacco in the case of non-filtered cigarettes. The recessed end of the polymer cigarette substitute prevents the tongue or lips from coming into contact with the punctured or severed opening.

A tool 36 is contemplated to be included with each pack of nicotine inhaler cigarette substitutes. The tool 36 consists of a separate plastic injection molded tube 38 that has a supportive cylindrical cavity 40, open at one end. The cavity 40 has an inner diameter slightly larger that the outer diameter of the cigarette substitute tube 10. With this tool 36, the cylindrical supportive cavity 40 and the conically shaped end walls 24, 26 form constraints concentrically about the cylindrical wall 12. It is this concentric system that allows all force to be directed and contained forward without lateral movement to enable easy hole punching.

The supportive cylindrical cavity 40 has a centric spike 42 in the cylindrical cavity 40 facing the open end. The spike is shown as a sharp conical element which could also be a needle, nail or screw with a sharp tip. The spike 42 can be molded or affixed by any means within the center of the supportive cylindrical cavity 40. The base of the spike 42 is approximately 0.125" in diameter. Any diameter sufficient to allow proper air flow through the tube once punctured may be used. The tool 36 has a terminal surface 44 across the supportive cylindrical cavity 40 within the tube 38 so that the spike 42 will only puncture and penetrate the tube 10 a sufficient distance to create the proper air flow hole desired.

The puncture tool 36 may also be included as an integrally molded part of a package 46 containing the cigarette substitute tubes 10; or the tool 36 may be a separate unit that is permanently attached to the package 46 itself. The length of the puncture tool tube 38 is contemplated to be any length practical but must be ½" or longer to facilitate the safety feature of the spike portion being recessed away from the user's touch during use.

The puncture tool 36 can be the same length as the tubes 10 so all may be conveniently included within each pack of cigarette substitutes but can be made to any size sufficient to serve its function. Thus for use, one inserts a cigarette tube within the puncture tool tube 38, pushes and the hole is easily punctured. This is repeated for the reverse side of the tube. The spike is positioned well below the face of the tool cavity 40 so a finger cannot be inserted within the tube. With an ID of approximately 0.250"-0.380" on the tool cavity 40, it would not be possible to insert ones finger into a hole that small beyond ¼". This is a safe, fast and simple tool included to facilitate the process of easily and quickly puncturing both ends of the tube to allow air flow and use of the product.

Thus, a new self contained, hermetically sealed, cigarette shaped nicotine inhaler tube is created that has no puncture area exposed to the body and includes a method for anyone to easily and quickly affect the puncturing required to release nicotine vapors from the liquid nicotine saturated filler contained within the tube to the user. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. A nicotine inhaler comprising
    a tube including a cylindrical wall of 0.25 to 0.35 inches in diameter and first and second end walls integral with the cylinder wall, the tube being impermeable to nicotine, the first end wall defining a first truncated conical wall extending inwardly from the cylindrical wall and forming a first truncated conical recess extending into the tube 0.25 to 0.75 inches to form a user mouthpiece on the tube at the first end wall;
    a filler within the tube able to carry nicotine;
    nicotine within the tube.

2. The nicotine inhaler of claim 1, the second end wall defining a second truncated conical wall extending inwardly from the cylindrical wall and forming a second truncated conical recess extending into the tube 0.25 to 0.75 inches to form a user mouthpiece on the tube at the second end wall.

3. The nicotine inhaler of claim 1, the tube having a sole fabricated fused joint between the first and second ends of the tube.

4. A nicotine inhaler system comprising
    the nicotine inhaler of claim 1;
    a tool including a supportive cylindrical cavity having an opening at one end, the cavity closely receiving the tube with the first end wall proximal the cavity, a tapered solid spike in the supportive cylindrical cavity facing the opening, the tapered spike being aligned with the end of the first truncated conical recess with the first end of the tube inserted in the cavity.

5. The system of claim 4, the tapered spike not extending the full length of the cavity.

6. A nicotine inhaler comprising
    a tube including a cylindrical wall of 0.25 to 0.35 inches in diameter and first and second end walls integral with the cylinder wall, the tube being impermeable to nicotine, the first end wall defining a first truncated conical wall extending inwardly from the cylindrical wall and forming a first truncated conical recess extending into the tube 0.35 to 0.75 inches to form a user mouthpiece on the tube at the first end wall, the first truncated conical wall having a wall thickness thinner than the wall thickness of the cylindrical wall;
    a filler within the tube able to carry nicotine;
    nicotine within the tube.

7. The nicotine inhaler of claim 6, the second end wall defining a second truncated conical wall extending inwardly from the cylindrical wall and forming a second truncated conical recess extending into the tube 0.25 to 0.75 inches to form a user mouthpiece on the tube at the second end wall.

8. The nicotine inhaler of claim 6, the tube having a sole fabricated fused joint between the first and second ends of the tube.

9. A nicotine inhaler system comprising
    the nicotine inhaler of claim 6;
    a tool including a supportive cylindrical cavity having an opening at one end, the cavity closely receiving the tube with the first end wall proximal the cavity, a tapered solid spike in the supportive cylindrical cavity facing the opening, the tapered spike being aligned with the end of the first truncated conical recess with the first end of the tube inserted in the cavity.

10. The system of claim 9, the tapered spike not extending the full length of the cavity.

* * * * *